United States Patent
Seltmann et al.

(10) Patent No.: US 10,405,929 B1
(45) Date of Patent: Sep. 10, 2019

(54) ATTACHMENT MECHANISM FOR SURGICAL TOOL TRACKING SYSTEM

(71) Applicants: Bradley S. Seltmann, Maitland, FL (US); James Fryzel, Oviedo, FL (US)

(72) Inventors: Bradley S. Seltmann, Maitland, FL (US); James Fryzel, Oviedo, FL (US)

( * ) Notice: Subject to any disclaimer, the term of this patent is extended or adjusted under 35 U.S.C. 154(b) by 362 days.

(21) Appl. No.: 15/353,970

(22) Filed: Nov. 17, 2016

Related U.S. Application Data

(60) Provisional application No. 62/256,789, filed on Nov. 18, 2015.

(51) Int. Cl.
*A61B 34/20* (2016.01)
*A61B 17/16* (2006.01)

(52) U.S. Cl.
CPC .......... *A61B 34/20* (2016.02); *A61B 17/1617* (2013.01)

(58) Field of Classification Search
CPC ...... A61B 17/16; A61B 17/1613–1633; A61B 17/1662–17/1693; A61B 34/20; A61B 34/30
See application file for complete search history.

(56) References Cited

U.S. PATENT DOCUMENTS

| | | | |
|---|---|---|---|
| 6,021,343 A * | 2/2000 | Foley ..................... | A61B 17/16 600/417 |
| 6,887,245 B2 | 5/2005 | Kienzle, III | |
| 7,166,114 B2 * | 1/2007 | Moctezuma De La Barrera ........ | G16H 40/40 606/130 |
| 7,771,436 B2 * | 8/2010 | Moctezuma De La Barrera ........ | A61B 90/36 600/424 |
| 9,345,552 B2 * | 5/2016 | Janik ................ | A61B 17/32002 |
| 9,877,786 B2 * | 1/2018 | Zastrozna .......... | A61B 17/1703 |
| 2001/0034530 A1 * | 10/2001 | Malackowski ........ | A61B 90/36 606/130 |
| 2002/0016599 A1 * | 2/2002 | Kienzle, III ....... | A61B 17/1703 606/130 |
| 2004/0054489 A1 * | 3/2004 | Moctezuma De La Barrera ........ | G16H 40/40 702/105 |
| 2004/0127888 A1 * | 7/2004 | O'Neil ............... | A61B 17/1622 606/1 |
| 2004/0230200 A1 | 11/2004 | Peterson | |
| 2005/0216032 A1 * | 9/2005 | Hayden .................. | A61B 17/17 606/130 |
| 2006/0142656 A1 * | 6/2006 | Malackowski .... | A61B 17/1626 600/424 |

(Continued)

*Primary Examiner* — Eric S Gibson
(74) *Attorney, Agent, or Firm* — Allen Dyer Doppelt & Gilchrist PA

(57) ABSTRACT

An attachment mechanism for a rotating surgical tool includes a mounting body defining a tool passage therein and configured for connection to a non-rotational component of the surgical tool, such that the tool passage is concentric about a rotational component of the surgical tool. The attachment mechanism further includes a ring arranged around the tool passage and rotatably connected to the mounting body. A mounting arm is attached to the ring such that rotation of the ring relative to the mounting body sets a desired circumferential position of the mounting arm relative to the tool passage, the mounting arm being configured to receive a tracking system emitter. An engagement mechanism is operable between the ring and the mounting body to maintain the desired circumferential position of the mounting arm.

7 Claims, 5 Drawing Sheets

(56) References Cited

U.S. PATENT DOCUMENTS

| | | | |
|---|---|---|---|
| 2007/0175489 A1* | 8/2007 | Moctezuma De La Barrera | G16H 40/40 128/898 |
| 2008/0009697 A1* | 1/2008 | Haider | A61B 17/15 600/407 |
| 2008/0183189 A1* | 7/2008 | Teichman | A61B 17/1655 606/130 |
| 2009/0299439 A1* | 12/2009 | Mire | A61B 17/1626 607/60 |
| 2010/0241129 A1* | 9/2010 | Markey | A61B 17/1626 606/104 |
| 2011/0264107 A1* | 10/2011 | Nikou | A61B 17/1622 606/130 |
| 2011/0313281 A1* | 12/2011 | Grinberg | A61B 17/16 600/424 |
| 2012/0022357 A1* | 1/2012 | Chang | A61B 6/022 600/407 |
| 2013/0060278 A1* | 3/2013 | Bozung | A61B 17/32002 606/205 |
| 2013/0096574 A1* | 4/2013 | Kang | A61B 17/1622 606/130 |
| 2013/0261609 A1* | 10/2013 | Dicorleto | A61B 17/1622 606/1 |
| 2014/0039517 A1* | 2/2014 | Bowling | B25J 13/00 606/130 |
| 2014/0180290 A1* | 6/2014 | Otto | A61B 17/1703 606/80 |
| 2014/0276943 A1* | 9/2014 | Bowling | A61B 17/16 606/130 |
| 2016/0278939 A1* | 9/2016 | Siccardi | A61B 17/1666 |
| 2017/0000572 A1* | 1/2017 | Moctezuma De La Barrera | A61B 34/20 |
| 2017/0150975 A1* | 6/2017 | Bozung | A61B 34/20 |
| 2017/0258532 A1* | 9/2017 | Shalayev | A61B 17/1624 |
| 2018/0125507 A1* | 5/2018 | Park | A61B 17/32 |
| 2019/0090966 A1* | 3/2019 | Kang | A61B 17/1671 |

* cited by examiner

ATTACHMENT MECHANISM FOR SURGICAL TOOL TRACKING SYSTEM

CROSS-REFERENCE TO RELATED APPLICATION

This application claims the benefit of U.S. Provisional Patent Application Ser. No. 62/256,789, filed on Nov. 18, 2015, the contents of which are herein incorporated by reference in their entirety.

FIELD OF THE INVENTION

The present invention relates to systems and methods for tracking surgical tools, and more particularly, to an attachment mechanism for facilitating attachment of a tracking device to a rotating surgical tool.

BACKGROUND OF THE INVENTION

Accurate tracking of the motion into a patient's body of a surgical tool, for instance, a drill bit, is crucial for ensuring appropriate utilization of the tool during surgery. Current surgical tool tracking systems typically make use of pre-operative techniques, such as MRI or CT scans, in combination with intra-operative techniques, for instance, X-ray imaging. Such techniques, however, are quite cumbersome. For example, the techniques increase radiation exposure to surgeon and patient, and ultimately, only provide two-dimensional spatial information. Some current surgical tool tracking systems also use video cameras or other localizing devices to track the movement of surgical tools in three-dimensional space. However, further improvements are possible to develop a tracking system that can be incorporated with any surgical tool and accurately track its motion.

SUMMARY OF THE INVENTION

In view of the foregoing, it is an object of the present invention to provide an attachment mechanism for a rotating surgical tool. The attachment mechanism includes a mounting body defining a tool passage therein and configured for connection to a non-rotational component of the surgical tool, such that the tool passage is concentric about a rotational component of the surgical tool. The attachment mechanism further includes a ring arranged around the tool passage and rotatably connected to the mounting body. A mounting arm is attached to the ring such that rotation of the ring relative to the mounting body sets a desired circumferential position of the mounting arm relative to the tool passage, the mounting arm being configured to receive a tracking system emitter. An engagement mechanism is operable between the ring and the mounting body to maintain the desired circumferential position of the mounting arm.

According to another embodiment of the present invention, a method for tracking a spatial location of a surgical tool includes connecting a tracking system emitter to a mounting arm of an attachment mechanism connected to a non-rotational component of the surgical tool, such that tool passage of a mounting body of the attachment mechanism is concentric with a rotational component of the surgical tool. The mounting arm of an attachment mechanism is rotated via a ring extending around the tool passage to set a desired circumferential position of the tracking system emitter. The spatial location of the tracking system emitter is tracked using a localizer in the vicinity thereof.

These and other objects, aspects and advantages of the present invention will be better understood in view of the drawing and following detailed description of preferred embodiments.

DETAILED DESCRIPTION OF PREFERRED EMBODIMENTS

Figure 1:
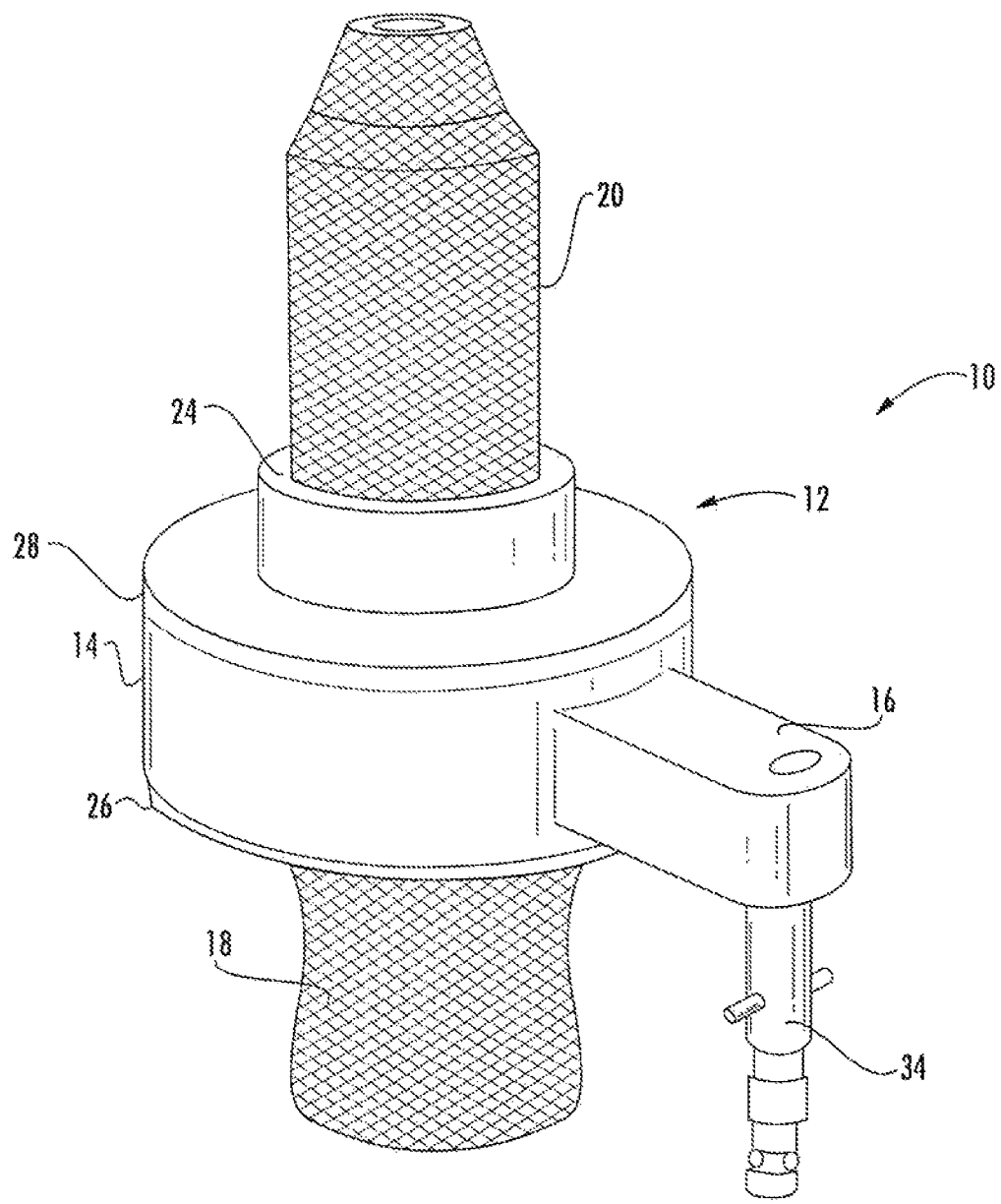
FIG. 1 is a perspective view of an attachment mechanism connected about a rotational component of a surgical tool, according to an embodiment of the presented invention.
Figure 2:
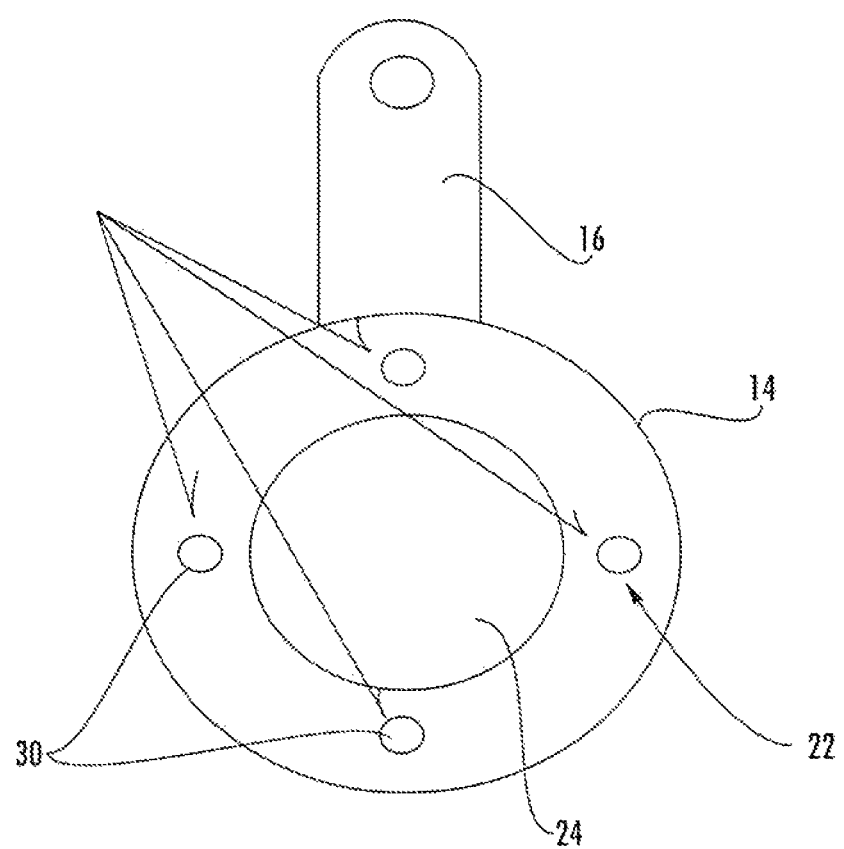
FIG. 2 is an end view of a ring of the attachment mechanism of FIG. 1.
Figure 3:
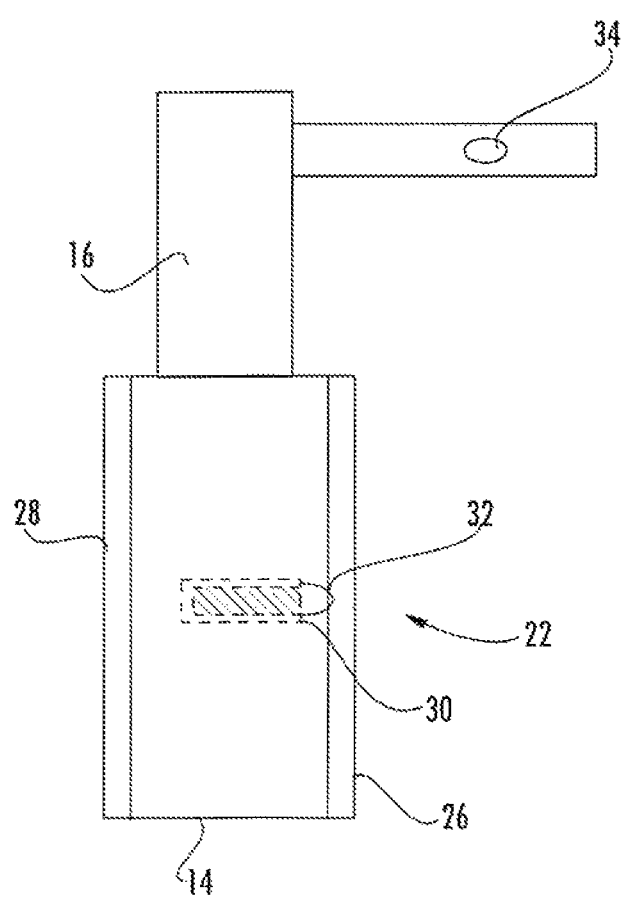
FIG. 3 is a partial sectional view the attachment mechanism of FIG. 1, with hidden components shown in broken lines.

Referring to FIGS. 1-3, according to an embodiment of the present invention, an attachment mechanism 10 for a surgical tool includes a tool mounting body 12, a ring 14, and a tracking device mounting arm 16. The tool mounting body 12 is configured for connection to a non-rotational component 18 of the surgical tool 20, such as a tool housing, concentric about a rotational component 20, such as a chuck bit or shaft. The mounting body 12 connects to the non-rotational component 18 so as to avoid rotation with the rotational component 20, while the ring 14 and mounting arm 16 can be selectively rotated relative to the mounting body 12, allowing a desired circumferential position of the mounting arm 16 to be set. An engagement assembly 22 is advantageously provided to maintain the desired circumferential position, once set.

In the depicted embodiment, the mounting body 12 defines a tool passage 24 through which the rotational component 20 passes, the tool passage 24 preferably being coaxial with the rotation component 20. The mounting body 12 further includes first and second plates 26, 28, arranged on opposite axial ends of the ring 14 and through which the tool passage 24 extends. At least one of the plates 26, 28 is affixed (e.g., welded) to the non-rotational component 18, and therefore does not rotate with the rotational component 20 (e.g., a shaft) while the tool is in use. The mounting body 12 is preferably generally cylindrical and made of steel or another suitable material.

The ring 14 is mounted coaxially about the rotating component 20 and thus rotates relative to the mounting body 12. In the depicted embodiment, the ring 14 is mounted between the first and second plates 26 and 28. The rotational position of the ring 14 is maintained by frictional or other engagement generated by the engagement assembly 22 relative to the mounting body 12. The ring 14 is preferably made of steel or another suitable material.

The engagement assembly 22 is configured to maintain the ring 14 in a desired circumferential position. For example, the engagement assembly 22 can include a plurality of locking members 30, such as spring screws, ball spring plungers, and/or other biased engagement mechanisms, installed on facing surfaces of the mounting body 12 and the ring 14 to and generating mutual engagement therebetween.

In the depicted embodiment, the four circumferentially spaced locking members 30 are installed in the ring 14 and extend toward the mounting body 12. Circumferentially spaced detents 32 can be formed on a facing surface of the second plate 28, which provides positions enhanced engagement. Other types of torquing and/or tensioning mechanisms can also be used to prevent rotation of the ring 14 once a desired circumferential position is found.

The mounting arm 16 extends radially outward from the ring 14 and preferably includes a mounting adapter 34 at a distal end thereof configured to receive a tracking system emitter. The mounting arm 16 rotates around the mounting body 12 as the ring 14 rotates. As such, the circumferential position of the mounting arm 16 relative to the mounting body 12 can be adjusted by rotating the ring 14 and maintained via the engagement assembly 22. The mounting arm 16 preferably has an elongated shape and is made of steel or another rigid material.

The various parts of the attachment mechanism 10 can be varied in size to suit the shape and size of the surgical tool to which it is attached. The attachment mechanism 10 can be made of steel, other appropriate metal alloys, plastic or a combination thereof.

Figure 4:
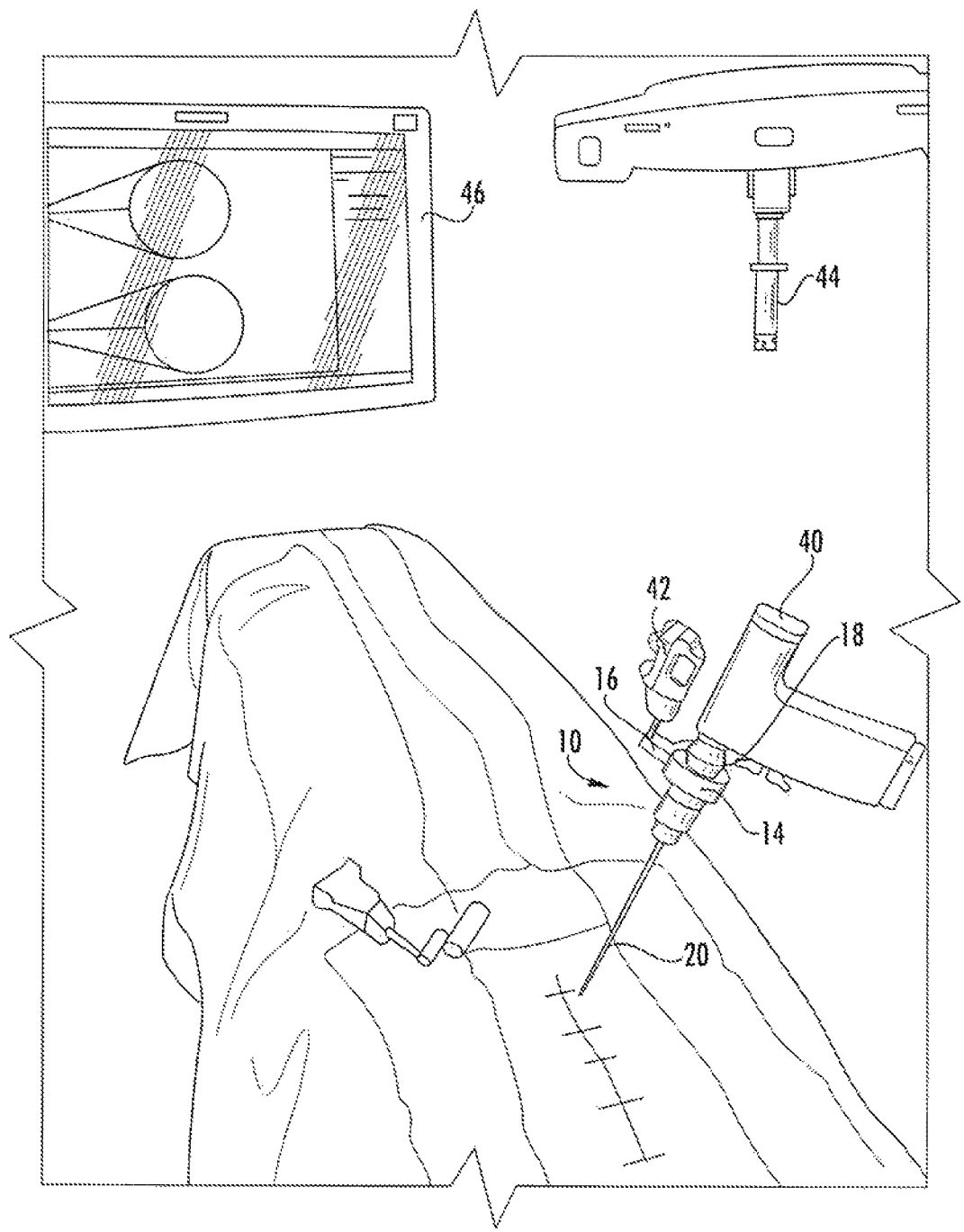
FIG. 4 is an overview of a surgical tool tracking system, including the attachment mechanism of FIG. 1 in use on a surgical drill.

FIG. 4 illustrates the attachment mechanism 10 attached to a surgical drill 40 in a spine surgery environment. Specifically, one or more emitters 42 are mounted on the mounting arm 16 to facilitate determination of the position of the rotational component 20 relative to a patient's body. As an example, the one or more emitters 42 can be visible-spectrum emitters, such as common light-emitting diodes (LEDs), or other suitable electromagnetic radiation emitters suitable for accurate locating by an appropriate localizer 44, for example, a camera. A surgeon holds the surgical drill 20 and adjust and lock the position of the mounting arm 16 as needed for a particular medical procedure. The localizer 44 monitors the position and movement of the emitters 42 relative to the patient's anatomical structures. A computer system can be used for automatic transformation of the data collected by the localizer 44 into three-dimensional coordinates of the emitters 42. Given information on the locations of the emitters 42 relative to the size and shape of the drill, the three-dimensional coordinates of the emitters 42 can be used for automatic transformation into the three-dimensional coordinates of the rotational component 20, providing information on the location of the rotational component 20 relative to the patients anatomical structures. The motion of the rotational component 20 relative to the patient's body can also be displayed on a monitor 46 for viewing by medical personnel.

Figure 5:
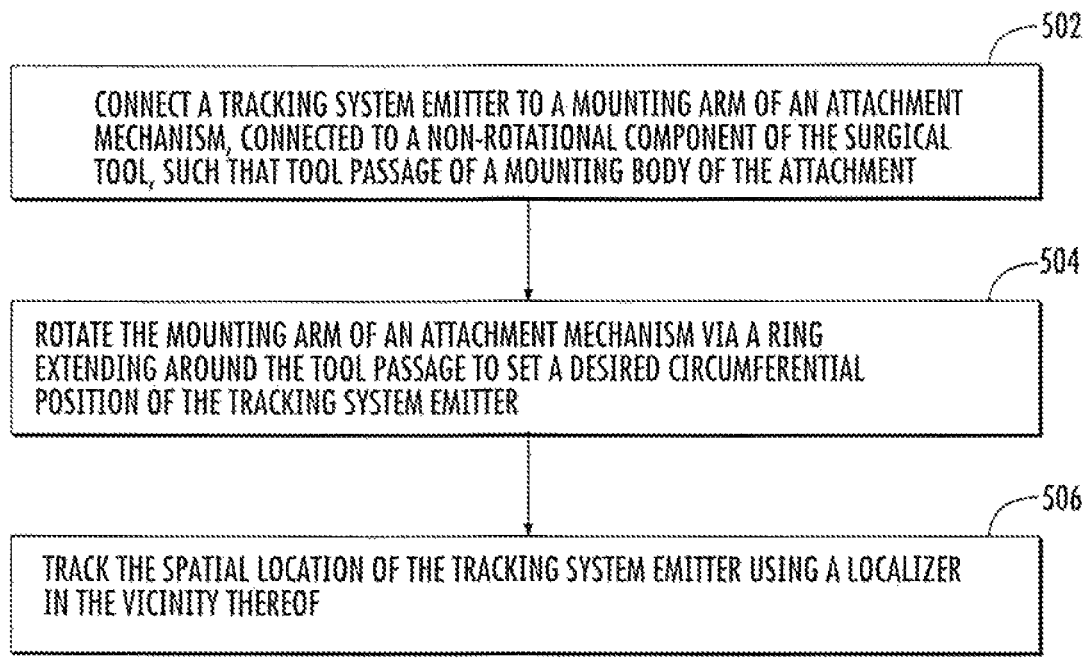
FIG. 5 is a flow chart illustrating a method of using the attachment mechanism, according to one embodiment of the present invention.

Referring to FIG. 5, a method for tracking a spatial location of a surgical tool includes, at step 502, connecting a tracking system emitter (e.g., emitter 42) to a mounting arm (e.g., mounting arm 16) of an attachment mechanism connected to a non-rotational component (e.g., non-rotational component 18) of the surgical tool (e.g., surgical drill 40), such that tool passage of a mounting body (e.g., mounting body 12) of the attachment mechanism is concentric with a rotational component of the surgical tool. At step 504, the mounting arm (e.g., mounting arm 16) of an attachment mechanism is rotated via a ring (e.g., ring 14) extending around the tool passage to set a desired circumferential position of the tracking system emitter (e.g., emitter 42). At step 506, the spatial location of the tracking system emitter is tracked using a localizer (e.g., localizer 44) in the vicinity thereof.

In general, the foregoing description is provided for exemplary and illustrative purposes; the present invention is not necessarily limited thereto. Rather, those skilled in the art will appreciate that additional modifications, as well as adaptations for particular circumstances, will fall within the scope of the invention as herein shown and described.

What is claimed is:

1. A method for tracking a spatial location of a surgical tool, the method comprising:
   connecting a tracking system emitter to a mounting arm of an attachment mechanism, connected to a non-rotational component of the surgical tool, such that tool passage of a mounting body of the attachment mechanism is concentric with a rotational component of the surgical tool;
   rotating the mounting arm of the attachment mechanism via a ring extending around the tool passage to set a desired circumferential position of the tracking system emitter; and
   tracking the spatial location of the tracking system emitter using a localizer in the vicinity thereof.

2. The method of claim 1, wherein the desired circumferential position is maintained by an engagement mechanism acting between the ring and the mounting body.

3. The method of claim 2, wherein setting the desired circumferential position includes rotating the mounting arm until a locking mechanism of the engagement mechanism engages a desired detent.

4. The method of claim 1, further comprising connecting the mounting body to the non-rotational component of the surgical tool.

5. The method of claim 1, wherein rotating the mounting arm of the attachment mechanism via the ring is performed after connecting the tracking system emitter to the mounting arm.

6. The method of claim 1, wherein the surgical tool is a surgical drill.

7. The method of claim 1, further comprising visually displaying a representation of the surgical tool relative to a patient's anatomy using three dimensional coordinates of the emitter obtained using the localizer.

* * * * *